United States Patent
Garrait et al.

(10) Patent No.: US 6,815,560 B1
(45) Date of Patent: Nov. 9, 2004

(54) PROCESS FOR THE PREPARATION OF HYDROXYMETHYLBUTYRIC ACID

(75) Inventors: Michel Garrait, Millery (FR); Georges Gros, Antony (FR)

(73) Assignee: Rhone-Poulenc Agro, Lyons Cedex (FR)

( * ) Notice: Subject to any disclaimer, the term of this patent is extended or adjusted under 35 U.S.C. 154(b) by 0 days.

(21) Appl. No.: 09/350,152

(22) Filed: Jul. 9, 1999

(30) Foreign Application Priority Data

Jul. 10, 1998 (FR) .............................. 98 08872

(51) Int. Cl.$^7$ .................. C07C 51/42; C07C 381/00
(52) U.S. Cl. ...................... 562/581; 562/580
(58) Field of Search ................. 562/581, 580

(56) References Cited

U.S. PATENT DOCUMENTS

| | | | |
|---|---|---|---|
| 2,938,053 A | | 5/1960 | Blake et al. |
| 4,524,077 A | * | 6/1985 | Reust et al. |
| 4,912,257 A | | 3/1990 | Hernandez et al. |
| 5,847,207 A | * | 12/1998 | Suchsland et al. |
| 5,998,664 A | * | 12/1999 | Hsu et al. |

FOREIGN PATENT DOCUMENTS

| | | |
|---|---|---|
| GB | 915193 | 1/1963 |
| WO | WO 96/40630 | 12/1996 |

\* cited by examiner

*Primary Examiner*—Ba K. Trinh
*Assistant Examiner*—Taylor V Oh
(74) *Attorney, Agent, or Firm*—Finnegan, Henderson, Farabow, Garrett & Dunner, LLP

(57) ABSTRACT

The invention relates to a new process for the preparation of hydroxymethylthiobutyric acid by sulphuric hydrolysis of hydroxymethylthiobutyronitrile.

19 Claims, No Drawings

PROCESS FOR THE PREPARATION OF HYDROXYMETHYLBUTYRIC ACID

The present invention relates to a new process for the preparation of 2-hydroxy-4-methylthiobutyric acid. It relates more particularly to a process for the hydrolysis of 2-hydroxy-4-methylthiobutyronitrile.

2-Hydroxy-4-methylthiobutyric acid is known to be used as a methionine analogue for feeding breeding animals and mainly, among these animals, poultry. This product is marketed under the trade marks Rhodimet AT 88™ or Alimet™.

It is known to prepare 2-hydroxy-4-methylthiobutyric acid by various processes for hydrolysing 2-hydroxy-4-methylthiobutyronitrile. The hydrolysis is carried out with an inorganic acid such as hydrochloric or sulphuric acid or it can also be carried out by enzymatic hydrolysis.

It is known according to Patent GB No. 915,193 to hydrolyse 2-hydroxy-4-methylthiobutyronitrile to 2-hydroxy-4-methylthiobutyric acid in the presence of an inorganic acid. That patent describes the continuous hydrolysis with a dilute sulphuric acid of 2-hydroxy-4-methylthiobutyronitrile and the organic acid obtained is recovered by extracting with an ether. Because the hydrolysis is carried out continuously in a stirred reactor, the process described in that patent gives an incomplete hydrolysis of the starting nitrile and consequently the presence of undesirable derivatives which cannot be given to animals without any risk.

It is also known from U.S. Pat. No. 4,524,077 to hydrolyse the same starting nitrile which is 2-hydroxy-4-methylthiobutyronitrile with sulphuric acid in two steps followed by an extraction of the hydrolysis medium with a solvent which is immiscible with water. The two-step process consists, in a first step, in using a sulphuric acid having a concentration between 50 and 70% by weight and at a temperature between 25 and 65° C. The introduction of 2-hydroxy-4-methylthiobutyronitrile is carried out for a period of 30 to 60 minutes and the hydrolysis of the nitrile to the corresponding amide is carried out for a period of 30 to 90 minutes. The 2-hydroxy-4-methylthiobutyramide is then converted to 2-hydroxy-4-methylthiobutyric acid by a subsequent hydrolysis step at a temperature situated in the range going from 70 to 120° C. The final hydrolysis step is carried out with an acid having a content of between 30 and 50% by weight. In practice, this content is obtained by addition of water. Under these conditions, 2-hydroxy-4-methylthiobutyramide is converted to 2-hydroxy-4-methylthiobutyric acid in 60 to 180 minutes. To convert the nitrile to an acid, the molar ratio of sulphuric acid relative to the nitrile is between 1 and 1.1.

U.S. Pat. No. 4,912,257 describes a process where the same nitrile, that is to say 2-hydroxy-4-methylthiobutyronitrile, is hydrolysed with sulphuric acid in such a manner that the molar ratio of sulphuric acid to 2-hydroxy-4-methylthiobutyronitrile is between 0.5 and 2 in order to form a reaction mixture containing 20–50% by weight of sulphuric acid. The mixture is maintained at a maximum temperature of 50° C. in a stirred reactor for 30–60 minutes. The second reaction step is carried out in a second reactor heated at a temperature between 60 and 140° C. for about 5 to 6 hours.

The patent application published under the number WO 96/40630 describes the same two-step hydrolysis reaction. The preferred ratio between sulphuric acid and 2-hydroxy-4-methylthiobutyronitrile is always, at the beginning of the initiation of the reaction, between 1.15 and 1.25 and then, when the reaction is in the stationary phase, between 0.9 and 1.2 and more preferably between 0.95 and 1.05. Many examples have been provided in order to vary this ratio. All the examples where the ratio is less than 0.88 show a 2-hydroxy-4-methylthiobutyronitrile conversion rate of less than 95%, which is considerably insufficient for industrial exploitation. In this patent application, the conclusion is that a sulphuric acid to nitrile ratio of between 1.0 and 1.2 should be used.

The disadvantage of using these quantities of sulphuric acid, of between 1.0 and 1.2 mol per mol of 2-hydroxy-4-methylthiobutyronitrile is the fact that at the end of the reaction, quantities of ammonium sulphates proportional to the quantities of sulphuric acid introduced are found. These high quantities of sulphate cause a major problem of industrial discharge which is increasingly difficult to solve. Moreover, the medium, being highly acidic; becomes very corrosive when hot and requires the use of exotic materials. From the reaction point of view, a ratio of 0.5 would appear to be sufficient, but it has proved chemically ineffective under the conditions used up until now. It would therefore appear to be impossible to go down as regards the molar ratio of the sulphuric acid relative to the nitrile below 0.88 which is the extreme limit which appears to be effective in the patent application mentioned above.

It has appeared quite surprisingly that it is possible to carry out the hydrolysis of 2-hydroxy-4-methylthiobutyronitrile to 2-hydroxy-4-methylthiobutyric acid with excellent yields with a molar ratio of sulphuric acid to 2-hydroxy-4-methylthiobutyronitrile of between 0.6 and 0.88. The use of a molar ratio of between 0.7 and 0.85 is preferred.

Preferably, the first step which is a reaction of hydration of 2-hydroxy-4-methylthiobutyronitrile to 2-hydroxy-4-methylthiobutyramide is carried out in a highly concentrated sulphuric acid medium in the presence of a sufficient quantity of water to carry out this reaction. The rate of this reaction is inversely proportional to the quantity of water. Thus, a quantity of water equal to one mol of water per mol of 2-hydroxy-4-methylthiobutyronitrile is necessary and a molar quantity of water of between 1 and 3.0 is preferred. A molar ratio between the water and 2-hydroxy-4-methylthiobutyronitrile of between 1 and 2.5 is still more preferably used.

This low concentration of water very greatly limits, during the first step, the successive hydrolysis of 2-hydroxy-4-methylthiobutyramide to 2-hydroxy-4-methylthiobutyric acid. It is thus preferable, during this first step, not to produce more than 5%, preferably less than 2% by weight of 2-hydroxy-4-methylthiobutyric acid. It is also preferable, during this first step, to obtain a concentration of 2-hydroxy-4-methylthiobutyramide greater than 95% by weight and preferably greater than 98% by weight. The operating conditions used during this first step are chosen within limits which do not lead to the production of 2-hydroxy-4-methylthiobutyric acid; it is thus preferable to work at a temperature of less than 60° C. and in particular of between 0° C. and 50° C. The reaction is preferably carried out in a continuous system of reactors in series with a residence time of between 15 minutes and 2 hours. The reaction pressure is preferably chosen between 0.01 and 3 bar.

The second step of the reaction is a hydrolysis of 2-hydroxy-4-methylthiobutyramide to 2-hydroxy-4-methylthiobutyric acid; it is carried out in the presence of the remaining quantity of sulphuric acid not consumed in the first step and in the presence of an additional quantity of water avoiding the separation of phases in the reaction medium. This step is preferably carried out in the presence of at least 28% by weight of water. As regards the reaction conditions, the work is preferably carried out at a temperature of between 90 and 130° C. Preferably, the procedure is carried out at a pressure of between 0.5 bar and a pressure of 5 bar. A pressure below atmospheric pressure makes it possible to remove traces of foul-smelling light gases for example of the dimethyl sulphide, dimethyl disulphide and methyl mercaptan type. The small excess of acid and the presence of ammonium hydrogen sulphate greatly limits the corrosive power of the medium at this temperature.

According to a better way of carrying out the process according to the invention, a concentrated solution of 2-hydroxy-4-methylthiobutyronitrile is introduced during the first step or an aqueous solution of 2-hydroxy-4-methylthiobutyronitrile is evaporated. When the procedure is carried out as described above, that is to say when the water contained in the aqueous solution of 2-hydroxy-4-methylthiobutyronitrile is evaporated, the water evaporated in the first step is advantageously recycled to the second step.

According to a better industrial means of carrying out the invention, the procedure is carried out according to the following sequence of steps starting with a concentrated or dilute solution of 2-hydroxy-4-methylthiobutyronitrile:

According to a first process for industrial implementation, a concentrated 2-hydroxy-4-methylthiobutyronitrile and concentrated $H_2SO_4$ solution, containing less than 20% by weight of water, is used.

The concentrated 2-hydroxy-4-methylthiobutyronitrile at about 80% by weight and the concentrated sulphuric acid at about 90% by weight are fed to an apparatus in which 2-hydroxy-4-methylthiobutyronitrile is hydrated. A solution containing 2-hydroxy-4-methylthiobutyramide is thus obtained. Water is added to this solution in order to avoid the precipitation of the ammonium hydrogen sulphate during the hydrolysis of 2-hydroxy-4-methylthiobutyramide. The solution obtained after hydrolysis contains 2-hydroxy-4-methylthiobutyric acid. The 2-hydroxy-4-methylthiobutyric acid is recovered from this solution.

It is, for example, possible to carry out the process continuously, semicontinuously or batchwise. When the process is carried out continuously, the apparatus used for the hydration of 2-hydroxy-4-methylthiobutyronitrile may comprise a first stirred reactor with an external recirculation loop which in particular serves to remove the calories released by the reaction. The hydration of 2-hydroxy-4-methylthiobutyronitrile may be completed in one or more stirred or piston reactors, preferably in series with the first reactor. A solution containing 2-hydroxy-4-methylthiobutyramide is thus obtained.

Water is added to this solution in order to avoid the precipitation of the ammonium hydrogen sulphate during the hydrolysis of 2-hydroxy-4-methylthiobutyramide. The apparatus used for the hydrolysis of 2-hydroxy-4-methylthiobutyramide may in particular comprise a first stirred reactor. The hydrolysis of 2-hydroxy-4-methylthiobutyramide may be completed according to a scheme for industrial implementation in one or more stirred or piston reactors in series with the first hydrolysis reactor.

According to a second process for implementation starting with dilute 2-hydroxy-4-methylthiobutyronitrile (for example 50%) and $H_2SO_4$, the process is carried out according to the following steps:

Concentrated 2-hydroxy-4-methylthiobutyronitrile at about 50% by weight and sulphuric acid are fed to an apparatus from which some of the water provided by the reagents is removed so as to return to the conditions described in the first process for implementation and 2-hydroxy-4-methylthiobutyronitrile is hydrated. A solution containing 2-hydroxy-4-methylthiobutyramide is thus obtained. Water, in particular the water previously removed, is added to this solution before hydrolysing 2-hydroxy-4-methylthiobutyramide. The solution obtained after hydrolysis contains 2-hydroxy-4-methylthiobutyric acid. The 2-hydroxy-4-methylthiobutyric acid is recovered from this solution.

It is possible, for example, to carry out this process continuously, semicontinuously or batchwise. When the process is carried out continuously, the apparatus used for the hydration of 2-hydroxy-4-methylthiobutyronitrile may comprise a first stirred reactor operating under reduced pressure. The calories released by the reaction are used to evaporate the water in excess relative to the conditions of the first process for carrying out the invention from a concentrated solution of 2-hydroxy-4-methylthiobutyronitrile. The process may be completed as indicated above.

According to a third process for carrying out the invention, the end of the second step is carried out under pressure. The hydrolysis of 2-hydroxy-4-methylthiobutyramide accelerates when the temperature increases. In order to exceed the boiling temperature of the medium, this step may be carried out under pressure.

The mixture obtained is then treated as described in U.S. Pat. No. 4,524,077 or U.S. Pat. No. 4,912,257. Thus, U.S. Pat. No. 4,912,257 describes following the hydrolysis step, a neutralizing step followed by a step for two-phase separation and for drying each of the two phases followed, for one of the phases, by a filtration step and, for the other, by a crystallization step. Adjusting to the final titre is done by addition of water.

U.S. Pat. No. 4,524,077 consists in carrying out a direct extraction from the hydrolysis medium with a solvent which is immiscible with water followed by evaporation of the said solvent in the presence of a quantity of water so as to reduce the appearance of a brown colour of the product obtained. The solvent is chosen in particular from methyl ethyl ketone, methyl isobutyl ketone, methyl tert-butyl ether, diisopropyl ether and diethyl carbonate.

The process described in U.S. Pat. No. 4,912,257 consists in carrying out a two-phase separation. A neutralizing agent of the ammonium hydroxide type is added to the medium resulting from the hydrolysis step. The medium separates into an organic phase (1) containing the desired acid and remaining salts. The aqueous phase (2) constituting the other phase contains essentially inorganic salts, especially ammonium sulphate and traces of organic acid. The two phases may be evaporated so as to remove the water in order to obtain an organic solution of 2-hydroxy-4-methylthiobutyric acid containing small quantities of ammonium sulphate which crystallizes, the latter is separated by filtration and 2-hydroxy-4-methylthiobutyric acid is adjusted to the desired commercial titre (88% by weight) by addition of water. Another solution consists in eliminating the inorganic salts present in the solution of 2-hydroxy-4-methylthiobutyric acid by adding an organic solvent which is only slightly miscible with water, such as in particular methyl ethyl ketone, methyl isobutyl ketone or diethyl carbonate. The release of an aqueous saline phase is then observed, the organic phase is freed of the solvent by evaporation and the final solution of 2-hydroxy-4-methylthiobutyric acid is adjusted to the commercial titre by addition of water.

The aqueous phase (2) is evaporated so as to precipitate the inorganic salts, essentially the ammonium sulphate which may be marketed as it is but which contains traces of foul-smelling organic derivatives. This aqueous phase may also be treated so as to deplete it of 2-hydroxy-4-methylthiobutyric acid. This depletion is achieved by addition of a solvent which is only slightly miscible with water chosen from methyl ethyl ketone, methyl isobutyl ketone and diethyl carbonate. The aqueous phase freed of its organic derivatives is dried so as to isolate the odourless inorganic salts which can be marketed directly. The organic phase for depletion is recycled, for example, with the 2-hydroxy-4-methylthiobutyric acid phase in order to recover the quantities of acid which are extracted from the saline aqueous phase.

The present invention will be described more fully with the aid of the following examples which should not be considered as limiting the invention.

COMPARATIVE EXAMPLE 1

Trial in a Closed Reactor, at a $H_2SO_4$/Cyanohydrin Ratio=1.2

Into a 250-ml glass reactor provided with:
a jacket whose temperature is regulated by circulation of oil,
a stirrer,
a condenser,
a thermocouple,
there are loaded a sediment of 89 g of cyanohydrin at 78 weight % in water and 45 g of water. Cyanohydrin at 52 wt. % in water is thus obtained.
65.5 g of sulphuric acid at 95% are gradually added (the sulphuric acid/cyanohydrin molar ratio is therefore equal to 1.2, the water/cyanohydrin molar ratio is equal to 7.11) while the temperature of the reaction mixture is maintained below 60° C.
Analysis of the medium shows that only 55% of the cyanohydrin is converted. The selectivities in relation to HMTBM and in relation to HMTBA are 91% and 9% respectively.
The mixture is heated to boiling temperature, at 112° C., in order to complete the reactions.
After 90 minutes under these conditions, analysis of the medium shows that:
 all the cyanohydrin is converted,
 the selectivities in relation to HMTBM and in relation to HMTBA are 0.4% and 99.6% respectively. The weight ratio of the ammonium sulphate produced relative to the HMTBA is 1.05.

COMPARATIVE EXAMPLE 2

Comparative Trial in a Closed Reactor, at a $H_2SO_4$/Cyanohydrin Ratio=0.81

Into a glass reactor provided with:
a jacket whose temperature is regulated by circulation of oil,
a stirrer,
a condenser,
a thermocouple,
there are loaded a sediment of 60 g of cyanohydrin at 78 weight % in water and 60 g of water.
30 g of sulphuric acid at 95% are gradually added (the sulphuric acid/cyanohydrin molar ratio is therefore equal to 0.81 and the water/cyanohydrin molar ratio is equal to 44.27) while the temperature of the reaction mixture is maintained below 60° C.
The reaction medium being heterogeneous, 210 g of water are added in order to obtain a homogeneous mixture. The medium is maintained for 30 minutes at 60° C. Analysis of the medium shows that:
 15% of the cyanohydrin is converted,
 the selectivities in relation to HMTBM and in relation to HMTBA are 64% and 36% respectively.
The mixture is heated to boiling temperature, at 104° C. After 160 minutes under these conditions, analysis of the medium shows that:
 only 29% of the cyanohydrin is converted,
 the selectivities in relation to HMTBM and in relation to HMTBA are 2% and 98% respectively. The weight ratio of the ammonium sulphate produced relative to the HMTBA is 0.72.

EXAMPLE 1

Trial in a Closed Reactor, at a $H_2SO_4$/Cyanohydrin Ratio=0.8 (JPZ 262)

Into a 250-ml glass reactor provided with:
a jacket whose temperature is regulated by circulation of oil,
a stirrer,
a condenser,
a thermocouple,
there is loaded a sediment of 60 g of cyanohydrin at 78 weight %.
30 g of sulphuric acid at 95% are gradually added (the sulphuric acid/cyanohydrin molar ratio is therefore equal to 0.8, the water/cyanohydrin molar ratio is therefore equal to 2.29) while the temperature of the reaction mixture is maintained below 40° C.
The medium is maintained for 30 minutes at 35° C. Analysis of the medium shows that:
 all the cyanohydrin is converted,
 the selectivities in relation to HMTBM and in relation to HMTBA are 99 and 1% respectively. 40 g of water are added and the mixture is heated to boiling temperature, at 110° C.
After 120 minutes under these conditions, analysis of the medium shows that:
 all the cyanohydrin is converted,
 the selectivities in relation to HMTBM and in relation to HMTBA are 0.3% and 99.7% respectively. The weight ratio of the ammonium sulphate produced relative to the HMTBA is 0.72.

EXAMPLE 2

Trial in a Closed Reactor, at a $H_2SO_4$/Cyanohydrin Ratio=0.7

Into a 150-ml glass reactor provided with:
a jacket whose temperature is regulated by circulation of oil,
a stirrer,
a condenser,
a thermocouple,
there is loaded a sediment of 75.5 g of cyanohydrin at 78 weight % in water.
32.2 g of sulphuric acid at 95% are gradually added while the temperature of the reaction mixture is maintained below 40° C. (the sulphuric acid/cyanohydrin molar ratio is therefore equal to 0.69, the water/cyanohydrin molar ratio is equal to 2.25).

The temperature is maintained at 40° C. for 15 minutes. Analysis of the medium shows that all the cyanohydrin was converted. The selectivities in relation to HMTBM and HMTBA are 98% and 2%.

55.5 g of water are added and the mixture is heated to boiling temperature, that is to say 107° C., in order to hydrolyse the HMTBM to HMTBA.

After two hours under these conditions, analysis of the medium shows that the selectivities in relation to HMTBM and in relation to HMTBA are 2% and 98%. The weight ratio of the ammonium sulphate produced relative to the HMTBA is 0.61.

EXAMPLE 3

Trial in a Closed Reactor, at a $H_2SO_4$ Cyanohydrin Ratio=0.8 (End of Reaction Under Pressure)

Into a 250-ml glass reactor provided with:

a jacket whose temperature is regulated by circulation of oil, a stirrer, a condenser, a thermocouple, there is loaded a sediment of 102.3 g of cyanohydrin at 78 weight % in water.

50 g of sulphuric acid at 95% are gradually added while the temperature of the reaction mixture is maintained below 40° C. (the sulphuric acid/cyanohydrin molar ratio is therefore equal to 0.8, the water/cyanohydrin molar ratio is equal to 2.28). The temperature is maintained at 40° C. for 15 minutes. Analysis of the medium shows that all the cyanohydrin was converted. Essentially HMTBM is obtained.

50.2 g of water are added and the mixture is heated to 90° C. After 30 min under these conditions, the appearance of a precipitate is observed. This precipitate is redissolved by addition of 10.9 g of water.

After one hour at 90° C., analysis of the medium shows that the selectivities in relation to HMTBM and HMTBA are 6% and 94%.

The reactor is heated to 125° C. at a pressure of 2.5 bar. An analysis carried out after 30 minutes at 125° C. shows that the selectivities in relation to HMTBM and HMTBA are 0.3% and 99.7%. The weight ratio of the ammonium sulphate produced relative to the HMTBA is 0.70.

EXAMPLE 4

Trial in a Closed Reactor, at a $H_2SO_4$/Cyanohydrin Ratio=0.8 (Total Conversion HMTBN and HMTBM)

Into a 5-l glass reactor provided with:

a jacket whose temperature is regulated by circulation of oil, a stirrer, a condenser, a thermocouple, there is loaded a sediment of 768 g of cyanohydrin at 77 weight % in water.

380 g of sulphuric acid at 95% are gradually added while the temperature of the reaction mixture is maintained below 20° C. (the sulphuric acid/cyanohydrin molar ratio is therefore equal to 0.8, the water/cyanohydrin molar ratio is equal to 2.41). The mixture is heated to 40° C. and this temperature is maintained for 20 minutes. Analysis of the medium-shows that all the cyanohydrin was converted.

501 g of water are added and the mixture is heated to boiling temperature, at 110° C., for one hour. Analysis of the medium shows that the selectivities in relation to HMTBM and in relation to HMTBA are 0.4% and 99.6%. The weight ratio of the ammonium sulphate produced relative to the HMTBA is 0.70.

EXAMPLE 5

Trial in a Continuous Reactor Under Vacuum (12 torr), at a $H_2SO_4$/Cyanohydrin Ratio=0.78

A mixture consisting of 163 g/h of cyanohydrin at 80% and 62 g/h of water (which corresponds to 225 g/h of HMTBN at 58 weight %), on the one hand, and 80 g/h of sulphuric acid at 95%, on the other hand, are supplied.

The sulphuric acid/cyanohydrin molar ratio is therefore equal to 0.78.

The reactor temperature is maintained at 50° C. The pressure is set at 12 torr.

Under these conditions, it is observed that under a stationary regime:

65 g/h of water are evaporated and the water/cyanohydrin molar ratio is equal to 1.88, the conversion of cyanohydrin is 90%. The selectivities in relation to HMTBM and HMTBA are 98% and 2%.

The supply of the reagents is then stopped, the vacuum is stopped, the temperature regulation at 50° C. is maintained and the reaction medium is allowed to follow its course.

The conversion of the cyanohydrin is monitored:

2 minutes after the stoppage, the conversion of the cyanohydrin is 99%, 13 minutes after the stoppage, the conversion of the cyanohydrin is 100%. The selectivities in relation to HMTBM and HMTBA are 95 and 5%. The weight ratio of the ammonium sulphate produced relative to the HMTBA is 0.69.

The 65 g of water evaporated during the first part of the trial plus an additional 39 g of water are then added and the medium is heated to boiling temperature, at 110° C., for one hour. Analysis of the medium shows that the selectivities in relation to HMTBM and HMTBA are 0.4% and 99.6%.

EXAMPLE 6

Trial in a Continuous Reactor Under Vacuum (12 torr), at a $H_2SO_4$/Cyanohydrin Ratio=0.6

A mixture consisting of 165 g/h of cyanohydrin at 80% and 57 g/h of water, on the one hand, and 62 g/h of sulphuric acid at 95%, on the other hand, are supplied.

The sulphuric acid/cyanohydrin molar ratio is therefore equal to 0.6.

The reactor temperature is maintained at 50° C. The pressure is set at 12 torr.

Under these conditions, it is observed that under a stationary regime:

62 g/h of water are evaporated and the water/cyanohydrin molar ratio is equal to 1.71, the conversion of cyanohydrin is 80%. The selectivities in relation to HMTBM and HMTBA are 98% and 2%.

The supply of the reagents is then stopped, the vacuum is stopped, the temperature regulation at 50° C. is maintained and the reaction medium is allowed to follow its course.

The conversion of the cyanohydrin is monitored:

5 minutes after the stoppage, the conversion of the cyanohydrin is 98%, 20 minutes after the stoppage, the conversion of the cyanohydrin is 99.5%. The selectivities in relation to HMTBM and HMTBA are 95 and 5%. The weight ratio of the ammonium sulphate produced relative to the HMTBA is 0.52.

It is then possible, as in the preceding examples, to add water (for example the water evaporated in this step) and to heat the mixture to boiling temperature in order to carry out hydrolysis of the HMTBM thus formed to HMTBA.

What is claimed is:

1. A process for the hydrolysis of 2-hydroxy-4-methylthiobutyronitrile comprising:
   (a) hydrating 2-hydroxy-4-methylthiobutyronitrile in a sulphuric acid medium to produce 2-hydroxy-4-methylthiobutyramide, wherein the molar quantity of sulphuric acid relative to the 2-hydroxy-4-methylthiobutyronitrile is between 0.6 and 0.88 and the molar quantity of water to 2-hydroxy-4-methylthiobutyronitrile is between 1 and 3; and
   (b) hydrolyzing the 2-hydroxy-4-methylthiobutyroamide in the presence of an additional quantity of water to produce 2-hydroxy-4-methylthiobutyric acid in a reaction mass,
   wherein the hydrating step (a) is carried out at such a pressure that the temperature of the reaction medium does not exceed 60° C. by evaporating water and the hydrolyzing step (b) is not carried out until the reaction medium of the hydrating step (a) contains more than 98% by weight 2-hydroxy-4-methylthiobutyramide.

2. The process according to claim 1, wherein the molar quantity of sulphuric acid relative to the 2-hydroxy-4-methylthiobutyronitrile is between 0.7 and 0.85.

3. The process according to claim 1, wherein the molar quantity of water to 2-hydroxy-4-methylthiobutyronitrile is between 1 and 2.5.

4. The process according to claim 1, wherein during the hydrolyzing step (b) a sufficient quantity of water is added in order to maintain the reaction mass in a homogeneous form.

5. The process according to claim 4, wherein the minimum quantity of water added is 28% by weight relative to the reaction mass.

6. The process according to claim 1, wherein the hydrolyzing step (b) is carried out at temperature ranging between 90 and 130° C.

7. The process according to claim 1, wherein the hydrolyzing step (b) is carried out at pressure ranging between 0.5 and 5 bar.

8. The process according to claim 1, further comprising:
   supplying the 2-hydroxy-4-methylthiobutyronitrile as a concentrated feed stream during the hydrating step (a); and
   maintaining the molar quantity of water of 2-hydroxy-4-methylthiobutyronitrile between 1 and 3.

9. The process according to claim 3 further comprising:
   supplying the 2-hydroxy-4-methylthiobutyronitrile as a concentrated feed stream during the hydrating step (a); and
   maintaining the molar quantity of water of 2-hydroxy-4-methylthiobutyronitrile between 1 and 2.5.

10. The process according to claim 8 or 9, wherein the concentrated feed stream comprises about 80 wt. % 2-hydroxy-4-methylthiobutyronitrile.

11. The process according to claim 1 further comprising:
    supplying the 2-hydroxy-4-methylthiobutyronitrile as a dilute aqueous feed stream during the hydrating step (a); and
    maintaining the molar quantity of water to 2-hydroxy-4-methylthiuobutyronitrile between 1 and 3 by evaporating excess water.

12. The process according to claim 3 further comprising:
    supplying the 2-hydroxy-4-methylthiobutyronitrile as a dilute aqueous feed stream during the hydrating step (a); and
    maintaining the molar quantity of water to 2-hydroxy-4-methylthiobutyronitrile between 1 and 2.5 by evaporating excess water.

13. The process according to claim 11 or 12, wherein the dilute aqueous feed stream comprises about 50 wt. % 2-hydroxy-4-methylthiobutyronitrile.

14. The process according to claim 1, wherein the reaction medium of the hydrating step (a) contains less than 2% by weight of 2-hydroxy-4-methylthiobutyric acid.

15. The process according to claim 1, wherein step (a) is carried out at a pressure ranging between 0.01 and 3 bar.

16. The process according to claim 1, wherein step (a) is carried out at a temperature ranging between 0 to 50° C.

17. The process according to claim 1, wherein step (a) is completed by stopping the supply of reagents.

18. The process according to claim 1, wherein during step (a), water in excess is distilled off.

19. The process according to claim 18, wherein the distilled excess water in step (a) is recycled and used in the hydrolyzing step (b).

* * * * *